United States Patent [19]

Niimura et al.

[11] Patent Number: 4,507,237

[45] Date of Patent: Mar. 26, 1985

[54] 2-[(2-METHOXY-5-HALO)AZO]-1-H-IMIDAZOLES AND METHOD OF PRODUCTION OF 2-[(2-METHOXY)AZO]-1-H-IMIDAZOLES

[75] Inventors: Isao Niimura, Iwatsuki; Shigeo Maeda; Hideo Okazaki, both of Tokyo, all of Japan

[73] Assignees: Hodogaya Chemical Co., Ltd.; Mochida Seiyaku Kabushiki Kaisha, both of Tokyo, Japan

[21] Appl. No.: 173,359

[22] Filed: Jul. 29, 1980

[30] Foreign Application Priority Data

Jul. 30, 1979 [JP] Japan .................................. 54-97058

[51] Int. Cl.$^3$ ..................... C07C 107/04; C09B 29/01; C09B 29/36; A61K 31/655
[52] U.S. Cl. ....................................................... 260/157
[58] Field of Search ......................................... 260/157

[56] References Cited

U.S. PATENT DOCUMENTS

| | | | |
|---|---|---|---|
| 3,102,879 | 9/1963 | Baumann et al. | 260/157 |
| 3,173,907 | 3/1965 | Klingsberg et al. | 260/157 |
| 3,216,995 | 11/1965 | Baumann et al. | 260/157 |
| 3,294,777 | 12/1966 | Hansen et al. | 260/157 |
| 3,357,783 | 12/1967 | Wunderlich et al. | 260/157 X |
| 3,468,871 | 9/1969 | Leverenz et al. | 260/157 X |
| 3,981,885 | 9/1976 | Buchel et al. | 260/157 X |

OTHER PUBLICATIONS

Beilstein, "Handbuch der Organischen Chemie", vol. 24, 2nd Supplement, p. 37, (1954).

*Primary Examiner*—Floyd D. Higel
*Attorney, Agent, or Firm*—Parkhurst & Oliff

[57] ABSTRACT

There are disclosed azo compounds represented by the formula:

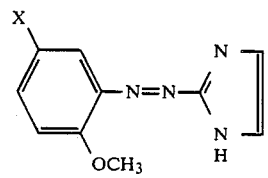

wherein X is hydrogen or halogen. The azo compounds are useful as precursors of disperse dyes and basic dyes and are effective for therapeutic treatment.

7 Claims, No Drawings

2-[(2-METHOXY-5-HALO)AZO]-1-H-IMIDAZOLES AND METHOD OF PRODUCTION OF 2-[(2-METHOXY)AZO]-1-H-IMIDAZOLES

BACKGROUND OF THE INVENTION

1. Field of the Invention

The present invention relates to novel azo compounds and a process for preparing the same and, more particularly, to the azo compounds and a process for preparing the azo compounds represented by the formula:

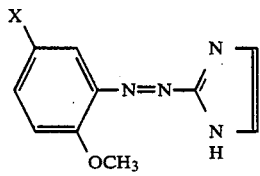

wherein X is hydrogen or halogen. The azo compounds are useful as precursors of disperse dyes and basic dyes and are effective for therapeutic treatment.

2. Brief Description of Prior Art

Generally, azo compounds are known to be useful as dyes including disperse and basic dyes. It is also known that imidazole can be a component to form various azo compounds. It is not known, however, that the azo compounds of the above formula can be basic and disperse dyes and that in particular they are effective for therapeutic treatment.

It is generally known that, when imidazole is used as a coupling component of azo compounds, it is usually employed in an amount of from about 1 to 1.5 moles based on a diazo component to which imidazole is coupled. In this case, however, the reaction permits the production of by-products in which the diazo component may be coupled to the 4-imidazolyl group or one more diazo components may be coupled to the 4-imidazolyl group. Accordingly, this reaction has a drawback in not providing the azo compounds in a pure form.

SUMMARY OF THE INVENTION

Accordingly, the object of the present invention is to provide novel azo compounds having the formula as represented hereinabove.

Another object of the present invention is to provide novel azo compounds which are useful as precursors for the production of disperse and/or basic dyes as well as effective as therapeutic agents.

A further object of the present invention is to provide a process for preparing the azo compounds having the formula as represented hereinabove without any substantial production of by-products.

Other objects, advantages and features of the present invention will become apparent during the course of the description which follows, but any modifications and improvements to be obviously made should be understood not to deviate from the scope of the present invention.

DETAILED DESCRIPTION OF THE INVENTION

The azo compounds according to the present invention include the azo compounds represented by the formula:

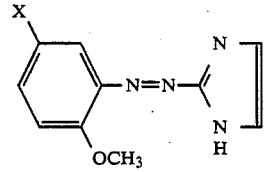

wherein X is hydrogen or halogen, and acid addition salts thereof. The term "halogen" is intended to mean chlorine, bromine, fluorine and iodine. The azo compounds may be converted in a conventional manner into their acid addition salts including an inorganic acid addition salt such as hydrochloride, hydrobromide, sulfate, nitrate and phosphate, and an organic acid addition salt such as acetate, succinate, maleate, oxalate and tartrate.

The azo compounds according to the present invention may be prepared by first reacting a 2-methoxyaniline or a reactive derivative thereof with sodium nitrite in the presence of hydrochloric acid and then coupling the resulting diazonium compound to imidazole in an amount of from approximately 5 to 10 moles based on the diazonium compound and, if desired, converting the azo compound into the corresponding acid addition salt.

The diazotization of a 2-methoxy aniline with a nitrite and hydrochloric acid may be carried out in conventional manner. The reaction conditions may be conventional and selected depending upon the type of reactants and other conditions.

The resulting diazonium compounds are then coupled to imidazole by reacting the former with the latter in an amount of from approximately 5 to 10 moles based on the diazonium compound. The resulting diazonium compounds may be used for the coupling reaction with or without being separated from the mixture where the diazonium compounds are formed. This reaction may be carried out in the presence of an alkali such as sodium hydroxide, potassium hydroxide or sodium carbonate or a buffer such as sodium acetate at a temperature of from 0° to 5° C. for about 1 hour. It is obvious that the reaction conditions with respect to the reaction time and temperature or the like may be varied depending upon the types of the reactants and solvents and the like.

The azo compounds according to the present invention exhibit pharmaceutical and therapeutic effects on hypotension, cardiac insufficiency or mucosa hyperemia.

It is shown that in particular, 2-[(2-methoxy-5-chlorophenyl)azo]-1H-imidazole and 2-[(2-methoxy-5-bromophenyl)azo]-1H-imidazole possess a diuretic activity about 10 times that of furosemide as a control, when applied to rats, and the other compounds are also higher in diuretic activity than furosemide. It is also seen that the azo compounds have an acute toxicity low enough to cause no problem in a usual application.

The following examples serve as an illustration of the present invention, but it should be understood that they are not intended at all in any sense to restrict the present invention thereto. In the examples, the unit "parts" is represented in parts by weight.

EXAMPLE 1

To a solution of 5.1 parts of 4-chloro-2-aminoanisole and 7.6 parts of 35% hydrochloric acid in 50 parts of water was added 15 parts of water containing 2.2 parts of sodium nitrite at 0°–5° C., and then the diazotization reaction was carried out by stirring the mixture at 0°–5° C. for 1 hour. The resulting diazonium salt solution was then added at 0°–5° C. to a solution of 20.4 parts of imidazole, 1.7 parts of sodium hydroxide and 2.5 parts of sodium acetate in 150 parts of water, and the mixture was stirred at the same temperature for 1 hour to complete the coupling reaction, thereby forming a crude yellow-orange product. The crude product was filtered, washed with water, and dried at 60° C. to provide 7.6 parts of the product.

This crude product (7 parts) was then recrystallized from n-propylalcohol to provide 4.9 parts of 2-[(2-methoxy-5-chlorophenyl)azo]-1H-imidazole as a yellow-orange columnar crystalline substance. It melted at 205° C. (decomposed), when measured in accordance with the designation of the Japanese Pharmacopeia and had a maximum ultraviolet absorption spectrum ($\lambda_{max}$) at 384 m$\mu$.

Elementary Analysis:

|  | C | H | N | Cl |
|---|---|---|---|---|
| Calculated (%) | 50.75 | 3.83 | 23.68 | 14.98 |
| Found (%) | 50.55 | 4.01 | 24.10 | 15.05 |

EXAMPLE 2

2.82 parts of 4-fluoro-2-aminoanisole and 5.2 parts of 35% hydrochloric acid were added to 50 parts of water. To this mixture was added 10 parts of water containing 1.38 parts of sodium nitrite at 0°–5° C., and then the mixture was stirred for 1 hour to effect diazotiaztion. The resulting diazonium salt solution was then added at 0°–5° C. to a solution of 13.6 parts of imidazole, 1.2 parts of sodium hydroxide and 1.64 parts of sodium acetate in 100 parts of water, and the coupling reaction was carried out by stirring the mixture for 1 hour. The yellow-orange azo compound precipitated in the reaction mixture was filtered, washed with water, and then dried at 60° C., thereby giving 4.3 parts of the crude azo compound.

The crude product (4 parts) was then recrystallized from n-butylalcohol to provide 2.9 parts of 2-[(2-methoxy-5-fluorophenyl)azo]-1H-imidazole as a yellow-orange acicular crystalline substance. It melted at 204° C. (decomposed), when measured in accordance with the designation of the Japanese Pharmacopeia and had a maximum ultraviolet absorption spectrum ($\lambda_{max}$) at 388 m$\mu$.

Elementary Analysis:

|  | C | H | N | F |
|---|---|---|---|---|
| Calculated (%) | 54.55 | 4.09 | 25.45 | 8.64 |
| Found (%) | 54.60 | 4.12 | 25.58 | 8.69 |

EXAMPLE 3

To a solution of 4.04 parts of 4-bromo-2-aminoanisole and 5.2 parts of 35% hydrochloric acid in 60 parts of water was added 10 parts of water containing 1.38 parts of sodium nitrite at 0°–5° C., and then the diazotization reaction was carried out by stirring the mixture at 0°–5° C. for 1 hour. The resulting diazonium salt solution was then added at 0°–5° C. to a solution of 9.53 parts of imidazole, 1.2 parts of sodium hydroxide and 1.64 parts of sodium acetate in 80 parts of water, and the mixture was stirred at the same temperature for 1 hour to complete the coupling reaction, thereby forming a crude yellow-orange product. The crude product was filtered and dried at 60° C. to provide 5.1 parts of the product.

This crude product (4 parts) was then recrystallized from ethyl acetate to provide 3.2 parts of 2-[(2-methoxy-5-bromophenyl)azo]-1H-imidazole as a yellow-orange acicular crystalline substance. It melted at 224.5° C. (decomposed), when measured in accordance with the designation of the Japanese Pharmacopeia and had a maximum ultraviolet absorption spectrum ($\lambda_{max}$) at 387 m$\mu$.

Elementary Analysis:

|  | C | H | N | Br |
|---|---|---|---|---|
| Calculated (%) | 42.70 | 3.20 | 19.93 | 28.44 |
| Found (%) | 42.71 | 3.27 | 19.90 | 28.39 |

EXAMPLE 4

The procedure of one of the above examples was followed except for the type of the reactants and solvents, thereby providing 2-[(2-methoxyphenyl)azo]-1H-imidazole as a yellow columnar crystalline substance, m.p. 152°–153° C.

EXAMPLE 5

To a solution of 4.98 parts of 4-iodo-2-aminoanisole and 5.2 parts of 35% hydrochloric acid in 70 parts of water was added 10 parts of water containing 1.38 parts of sodium nitrite at 0°–5° C., and then the diazotization reaction was carried out by stirring the mixture at 0°–5° C. for 1 hour. The resulting diazonium salt solution was then added at 0°–5° C. to a solution of 10.89 parts of imidazole, 1.2 parts of sodium hydroxide and 1.64 parts of sodium acetate in 80 parts of water, and the mixture was stirred at the same temperature for 1 hour to complete the coupling reaction, thereby forming a crude yellow-orange product. The crude product was filtered, washed with water, and dried at 60° C. to provide 5.9 parts of the product.

This crude product (4.5 parts) was then column-chromatographed on silica gel to provide 3.5 parts of 2-[(2-methoxy-5-iodophenyl)azo]-1H-imidazole as a yellow-orange columnar crystalline substance. It melted at 217.5° C. (decomposed), when measured in accordance with the designation of the Japanese Pharmacopeia and had a maximum ultraviolet absorption spectrum ($\lambda_{max}$) at 385 m$\mu$.

Elementary Analysis:

|  | C | H | N | I |
|---|---|---|---|---|
| Calculated (%) | 36.59 | 2.74 | 17.07 | 38.69 |
| Found (%) | 36.61 | 2.70 | 17.09 | 38.61 |

What is claimed is:
1. A compound represented by the formula:

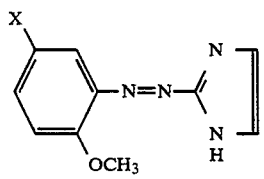

wherein X is halogen or an acid addition salt thereof.

2. The compound claimed in claim 1, wherein the compound is 2-[(2-methoxy-5-chlorophenyl)azo]-1H-imidazole.

3. The compound claimed in claim 1, wherein the compound is 2-[(2-methoxy-5-bromophenyl)azo]-1H-imidazole.

4. The compound claimed in claim 1, wherein the compound is 2-[(2-methoxy-5-iodophenyl)azo]-1H-imidazole.

5. The compound claimed in claim 1, wherein the compound is 2-[(2-methoxy-5-fluorophenyl)azo]-1H-imidazole.

6. A process for the high yield preparation of a compound of the formula

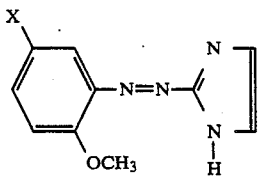

wherein X is a hydrogen or halogen atom, or an acid addition salt thereof, comprising
reacting a compound of the formula

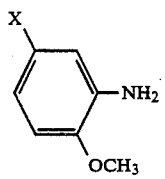

wherein X is as previously defined with a nitrite and hydrochloric acid to form a diazonium compound, and
reacting the resulting diazonium compound of the above reaction with imidazole in a quantity of about 5 to 10 moles of imidazole per mole of diazonium compound to give the compound of formula (I) in a high yield.

7. A process as claimed in claim 6, further comprising converting the compound of formula I into an acid addition salt thereof.

* * * * *

UNITED STATES PATENT AND TRADEMARK OFFICE
CERTIFICATE OF CORRECTION

PATENT NO.   :   4,507,237
DATED        :   March 26, 1985
INVENTOR(S)  :   Niimura et al.

It is certified that error appears in the above-identified patent and that said Letters Patent is hereby corrected as shown below:

On the cover sheet of the patent, the lefthand column, section "/75/ Inventors:" change "Okazaki, both" to --Okazaki; Ei Mochida, all--; change "Tokyo," to --Tokyo; Yasuo Suzuki, Kawaguchi; Haruo Ohnishi, Funabashi; Hiroshi Kosuzume, Yokohama,--.

On the cover sheet of the patent, the lefthand column, under heading "/30/ Foreign Application Priority Data", insert the following second line: "Jul. 30, 1979 /JP/ Japan ................ 54-97059".

Signed and Sealed this

Sixth Day of August 1985

[SEAL]

Attest:

DONALD J. QUIGG

Attesting Officer

Acting Commissioner of Patents and Trademarks